United States Patent [19]
Sarfarazi

[11] Patent Number: 5,962,230
[45] Date of Patent: Oct. 5, 1999

[54] DIAGNOSIS AND TREATMENT OF GLAUCOMA

[75] Inventor: Mansoor Sarfarazi, New Britain, Conn.

[73] Assignee: The University of Connecticut, Farmington, Conn.

[21] Appl. No.: 08/926,492

[22] Filed: Sep. 10, 1997

Related U.S. Application Data

[63] Continuation-in-part of application No. 08/800,036, Feb. 13, 1997, Pat. No. 5,830,661.
[51] Int. Cl.$^6$ .......................... C07H 21/04; C07H 21/02; C12Q 1/68; C12P 19/34
[52] U.S. Cl. .......................... 435/6; 435/91.1; 435/91.2; 536/23.1; 536/24.31; 536/24.33; 935/77; 935/78
[58] Field of Search .......................... 435/6, 91.2, 91.1; 536/23.1, 24.31, 24.33; 935/77, 78

[56] References Cited

FOREIGN PATENT DOCUMENTS

WO96/33287  10/1996  WIPO.

OTHER PUBLICATIONS

Ming, Y.T. et al., "Isolation and Characterization of the Human Cytochrome P450 CYP1B1 Gene," *J. Biol. Chem.* 271 (45):28324–28330.

Bejjani, B.A. et al., "Mutations in CYP1B1, the Gene for Cytochrome P4501B1, Are the Predominant Cause of Primary Congenital Glaucoma in Saudi Arabia," *Am. J. Hum. Genet.* 62: 325–333 (1998).

Leff, D.N., "New–Found Gene Enables Testing Infants for Inherited Blindness Disease", *BioWorld Today,* 8(53):1 (Mar. 19, 1997).

Stone, E.M., et al., "Identification of a Gene That Causes Primary Open Angle Glaucoma", *Science,* 275:668–670 (1997).

Vogel, G., "Glaucoma Gene Provides Light at the End of the Tunnel", *Science,* 275:621 (1997).

Stoilova, D., et al., "Localization of a Locus (GLC1B) for Adult–Onset Primary Open Angle Glaucoma to the 2cen–q13 Region", *Genomics,* 36:142–150 (1996).

Sarfarazi, M., et al., "Assignment of a Locus (GLC3A) for Primary Congenital Glaucoma (Buphthalmos) to 2p21 and Evidence for Genetic Heterogeneity", *Genomics,* 30:171–177 (1995).

Akarsu, A.N. et al., "A second locus (GLC3B) for primary congenital glaucoma (Buphthalmos) maps to the 1p36 region", *Human Molecular Genetics,* 5(8):1199–1203 (1996).

Akarsu, A.N. et al., "Exclusion of Primary Congenital Glaucoma (Buphthalmos) From Two Candidate Regions of Chromosome Arm 6p and Chromosome 11", *American Journal of Medical Genetics,* 61:290–292 (1996).

Stoilov, I., et al., "Fine Mapping of Primary Congenital Glaucoma (Buphthalmos) on 2p21 and Mutation Screening of Candidate Genes", *Am. J. Hum. Genet.* (*Supplement*) 59(3): Abstract 1366 p. A237 (1996).

Yilmaz, E., "Localization and Mutation Screening of a New Locus (GLC3B) for Primary Congenital Glaucoma (Buphthalmos) on 1p36", *Am. J. Hum. Genet.* (*Supplement*) 59(3): Abstract 1404 p. A243 (1996).

Stoilova, D. et al., "Assignment of a New Locus (GLC1B) for Adult–Onset Primary Open Angle Glaucoma to the 2cen–q13 Region", *Am. J. Hum. Genet.* (*Supplement*) 59(3): Abstract A1407A p. A244 (1996).

Bejjani, B.A. et al., "Mapping strategies in Primary Congenital Glaucoma (PCG)", *Am. J. Hum. Genet.* (*Supplement*) 59(3): Abstract 1216 p. A212 (1996).

Wiggs, J.L., et al., "The juvenile glaucoma gene on 1q21–q31 is not associated with adult–onset primary open angle glaucoma", *Am. J. Hum. Genet.* (*Supplement*) 59(3): Abstract 1393 p. A242 (1996).

Allingham, R.R. et al., "Genes linked to systemic hypertension (HTN) and non–insulin dependent diabetes mellitus (NIDDM) are not associated with Primary Open Angle", *Am. J. Hum. Genet.* (*Supplement*) 59(3): Abstract 2213 p. A380 (1996).

Raymond, V. et al., "Homozygotes for autosomal dominant open–angle glaucoma at the GLCIA locus", *Am. J. Hum. Genet.* (*Supplement*) 59(3): Abstract 1625 p. A280 (1996).

Richards, J.E. et al., "Juvenile glaucoma linked to GLC1A in a family of spanish origin", *Am. J. Hum. Genet.* (*Supplement*) 59(3): Abstract 2257 p. A387 (1996).

Booth, A.P., et al., "Physical and Genetic mapping of the juvenile–onset primary open–angle glaucoma locus", *Am. J. Hum. Genet.* (*Supplement*) 59(3):Abstract 2359 p. A404 (1996).

Sunden, S.L.F., et al., "Narrowing the GLC1A critical region using a late–onset autosomal dominant open angle glaucoma family", *Am. J. Hum. Genet.* (*Supplement*) 59(3): Abstract 1369 p. A238 (1996).

(List continued on next page.)

*Primary Examiner*—Stephanie W. Zitomer
*Attorney, Agent, or Firm*—Hamilton, Brook, Smith & Reynolds, P.C.

[57] ABSTRACT

Methods of diagnosing glaucoma, and particularly primary congenital glaucoma, by detecting mutations in a gene associated with glaucoma, such as the CYP1B1 gene, are disclosed. Methods include hybridization analysis, such as Southern or Northern analysis, which use hybridization of a mutant nucleic acid probe to the gene associated with glaucoma; direct mutation analysis by restriction digest; sequencing of the gene associated with glaucoma; hybridization of an allele-specific oligonucleotide with amplified genomic DNA; or identification of the presence of mutant proteins encoded by the gene associated with glaucoma. Kits for use in diagnosis of glaucoma are also described. Methods of treatment of glaucoma, including administration of the protein encoded by the gene associated with glaucoma; administration of genes, gene constructs, or other nucleic acid constructs; or administration of other therapeutic agents, are additionally described.

10 Claims, 3 Drawing Sheets

OTHER PUBLICATIONS

Graff, C. et al., "Confirmation of linkage to 1q21–31 in a Danish autosomal dominant juvenile–onset glaucoma family and evidence of genetic heterogeneity", *Human Genet.,* 96:285–289 (1995).

Morissette, J. et al., "A common gene for juvenile and adult onset primary open–angle glaucomas confines on chromosome 1q", *Am. J. Hum. Genet.,* 56:1431–1442 (1995).

Richards, J.E. et al., "Mapping of a gene for autosomal dominant juvenile–onset open–angle glaucoma to chromosome 1q", *Am. J. Hum. Genet.,* 54:62–70 (1994).

Seghatoleslami, M.R. et al., "Fine mapping of juvenile primary open angle glaucoma (POAG) on 1q21–q31 and exclusion of adult–POAG from the respective region", *Am. J. Hum. Genet.,* 55:Abstract 1179, p. A203 (1994).

Seghatoleslami, M.R., et al., "Exclusion mapping of the adult–onset primary open angle glaucoma (POAG)", *Invest. Ophthalmol. & Visual Science,* 36(4):Abstract 4792, p. S1034 (1995).

Sheffield, V.C. et al., "A collecion of tri– and tetranucleotide repeat markers used to generate high quality, high resolution human genomewide linkage maps", *Hum. Mol. Genet.,* 4:1837–1844 (1995).

Stoilova, D. et al., "Genetic linkage study of adult–onset primary open angle glaucoma", *Am. J. Hum. Genet.,* 57(4):Abstract 1895, p. A326 (1995).

Wiggs, J.L. et al., "Clinical features of five pedigrees genetically linked to the juvenile glaucoma locus on chromosome 1q21–q31", *Opthalmology,* 102:1782–1789 (1995).

Wiggs, J.L. et al., "Genetic linkage of autosomal dominant juvenile glaucoma to 1q21–q31 in three affected pedigrees", *Genomics,* 21:299–303 (1994).

Sutter, T.R. et al., "Complete cDNA Sequence of a Human Dioxin–inducible mRNA Identifies a New Gene Subfamily of Cytochrome P450 That Maps to Chromosome 2", *J. Biol. Chem. 269:*13092–13099 (1994).

Sarfarazi, M., "Recent Advances in Molecular Genetics of Glaucomas," *Humn. Mol. Genet.,* 6(10):1667–1677, 1997.

Stoilov, I. et al., "Identification of three different truncating mutations in cytochrome P4501B1 (CYP1B1) as the principal cause of primary congenital glaucoma (Buphthalmos) in families linked to the GLC3A locus on chromosome 2p21," *Hum. Mol. Genet.,* 4(4):641–647, 1997.

Stoilova, D. et al., "Identification of a new 'TIGR' mutation in a family with juvenile–onset primary open angle glaucoma," *Opthal. Genet.,* 18:109–118, 1997.

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (xi) SEQUENCE DESCRIPTION: SEQ ID NO:1:

GAGTGCAGGC AGA            13

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:2:

```
GGTTCCTGTT GACGTCTTG                                               19
```

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:3:

```
CTTCCAGTGC TCCGAGTAG                                               19
```

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:4:

```
GTGGTGCTGA ATGGCGAG                                                18
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:5:

```
TACTGCAGCC AGGGCATC                                                18
```

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:6:

```
GTGGCCAACG TCATGAGTG                                               19
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

```
TCATAAAGGA AGGCCAGGAC                                              20
```

(2) INFORMATION FOR SEQ ID NO:8:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:8:

AGACTCGAGT GCAGGCAG                                            18

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

TCCTCATCTC CGAAGATGGT                                        20

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:10:

CCTCCCAGAG GCTTTACCT                                         19

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

TAAGAATTTT GCTCACTTGC                                        20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

TCAATGTCAC TCTCAGAGAG                                        20

(2) INFORMATION FOR SEQ ID NO:13:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:13:

CGCAGGTCAG T                                                            11

(2) INFORMATION FOR SEQ ID NO:14:

(i) SEQUENCE CHARACTERISTICS:

(A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:14:

CCCAGCATGG                                                                  10

(2) INFORMATION FOR SEQ ID NO:15:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:15:

ACCAGGTAAA G                                                                11

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:16:

AACAGGTATC                                                                  10

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

CAAACAGGTA TCCTGATGTG                                                       20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:18:

GACAAGTTCT TGAGGCACTG C                                                     21

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:19:

ACGTTCTCCA AATCCAGCC                                                        19

(2) INFORMATION FOR SEQ ID NO:20:

(i) SEQUENCE CHARACTERISTICS:
        (A) LENGTH: 10 base pairs
        (B) TYPE: nucleic acid (C) STRANDEDNESS: single
        (D) TOPOLOGY: linear (xi) SEQUENCE DESCRIPTION: SEQ ID NO:20:

TCATGCCACC                                                                10

DIAGNOSIS AND TREATMENT OF GLAUCOMA

RELATED APPLICATION

This application is a Continuation-in-Part application of U.S. Ser. No. 08/800,036, filed Feb. 13, 1997, issued as U.S. Pat. No. 5,830,661, the entire teachings of which are incorporated herein by reference.

GOVERNMENT FUNDING

This invention was made with Government support under Contract No. EY-11095 awarded by the National Eye Institute and Contract No. MOI-RR-06192 awarded by the National Institutes of Health. The Government has certain rights in the invention.

BACKGROUND OF THE INVENTION

Glaucoma is a group of ocular disorders, characterized by degeneration of the optic nerve. It is one of the leading causes of blindness worldwide. One major risk factor for developing glaucoma is family history: several different inherited forms of glaucoma have been described.

Primary congenital or infantile glaucoma (gene symbol: GLC3) is an inherited disorder that accounts for 0.01–0.04% of total blindness. It is characterized by an improper development of the aqueous outflow system of the eye, which leads to elevated intraocular pressure, enlargement of the globe or cornea (i.e., buphthalmos), damage to the optic nerve, and eventual visual impairment. Pathogenesis of GLC3 remains elusive despite efforts to identify a single anatomic defect. At least two chromosomal locations associated with the disease have been identified: one locus at 2p21 (GLC3A) (Sarfarazi, M. et al., Genomics 30:171–177 (1995); and a second locus at 1p36 (GLC3B) (Akarsu, A. N. et al., Hum. Mol. Gen. 5(8):1199–1203 (1996)). Other specific loci, including a region of 6p and chromosome 11, have been excluded (Akarsu, A. N. et al., Am. J. Med. Genet. 61:290–292 (1996)).

Primary open angle glaucoma (gene symbol: GLC1) is a common disorder characterized by atrophy of the optic nerve resulting in visual field loss and eventual blindness. GLC1 has been divided into two major groups, based on age of onset and differences in clinical presentation.

Juvenile-onset primary open angle glaucoma (GLC1A) usually manifests in late childhood or early adulthood. The progression of GLC1A is rapid and severe with high intraocular pressure, is poorly responsive to medical treatment, and is such that it usually requires ocular surgery. GLC1A has been mapped to the q21–q31 region of chromosome 1, with genetic heterogeneity (Sheffield, V. C. et al., Hum. Mol. Genet. 4:1837–1844 (1995)).

Adult- or late-onset primary open angle glaucoma (GLC1B) is the most common type of glaucoma. It is milder and develops more gradually than juvenile-onset primary open angle glaucoma, with variable onset usually after the age of 40. GLC1B is associated with slight to moderate elevation of intraocular pressure, and often responds satisfactorily to regularly monitored medical treatment. However, because the disease progresses gradually and painlessly, it may not be detected until a late stage when irreversible damage to the optic nerve has already occurred. Linkage, haplotype and clinical data have assigned a locus for GLC1B to the 2cen-q13 region (Stoilova, D. et al., Genomics 36:142–150 (1996)), as well as a new locus 3q21–q22 (Sarfarazi, M. et al., submitted 1996), with further evidence for several other loci.

Because of the insidious nature of glaucoma, a need remains for a better and earlier means to diagnose or predict the likelihood of development of glaucoma, so that preventative or palliative measures can be taken before significant damage to the optical nerve occurs.

SUMMARY OF THE INVENTION

The invention pertains to methods of diagnosing or treating glaucoma. The methods of diagnosing glaucoma in an individual include detecting the presence of a mutation in a gene associated with the disease. The mutation can be the insertion or deletion of one or more nucleotides, resulting in a frame shift mutation; the change of at least one nucleotide, resulting in a change in the encoded amino acid; the change of at least one nucleotide, resulting in a premature stop codon; the insertion of one or several nucleotides, such as an insertion caused by unequal recombination or gene conversion, resulting in an interruption of the coding sequence of the gene; duplication of a part of the gene; transposition of all or a part of the gene; or rearrangement of all or a part of the gene. More than one mutation can be present in a gene associated with glaucoma. The mutations associated with glaucoma can be identified by numerous methods, such as Southern analysis of genomic DNA; amplification of genomic DNA followed by direct mutation analysis by restriction enzyme digestion; Northern analysis of RNA; gene isolation and direct sequencing; or analysis of the protein encoded by the gene associated with glaucoma.

For example, a sample of DNA containing the gene is obtained from an individual suspected of having glaucoma or of being a carrier for glaucoma (the test individual). The DNA is contacted with at least one mutant nucleic acid probe under conditions sufficient for specific hybridization of the gene to the mutant nucleic acid probe. The mutant nucleic acid probe comprises DNA, cDNA, or RNA of the gene, or a fragment of the gene, having at least one of the mutations described above, or an RNA fragment corresponding to such a cDNA fragment. The presence of specific hybridization of the mutant nucleic acid fragment to the mutant nucleic acid probe is indicative of a mutation in the gene that is associated with glaucoma. In another example, the DNA is contacted with a PNA probe under conditions sufficient for specific hybridization of the gene to the PNA probe; the presence of specific hybridization is indicative of a mutation in the gene that is associated with glaucoma.

Alternatively, direct mutation analysis by restriction digest of a sample of genomic DNA, RNA or cDNA from the test individual can be conducted, if the mutation results in the creation or elimination of a restriction site. The digestion pattern of the relevant DNA, RNA or cDNA fragment indicates the presence or absence of the mutation associated with glaucoma.

The presence of a mutation associated with glaucoma can also be diagnosed by sequence data. A sample of genomic DNA, RNA or cDNA from the test individual is obtained, and the sequence of the gene, or a fragment of the gene, is determined. The sequence of the gene from the individual is compared with the known sequence of the gene (the control sequence). The presence of a mutation, as described above, in the gene of the individual is indicative of the a mutation that is associated with glaucoma.

The invention additionally pertains to methods of diagnosing glaucoma in an individual by detecting alterations in expression of a protein encoded by the gene associated with glaucoma. The alteration in expression can be an alteration of the amount of protein expressed (a quantitative alteration), or an alteration of the composition of the protein expressed (a qualitative alteration), or both. An alteration in expression of the protein encoded by the gene associated with glaucoma in a test sample, as compared with expression of protein encoded by the gene associated with glaucoma in a control sample, is indicative of the disease. Alterations in expression of the protein can be assessed using standard techniques, such as Western blotting.

The invention additionally pertains to antibodies (monoclonal or polyclonal) to proteins encoded by mutated genes associated with glaucoma. These antibodies can also be used in methods of diagnosis. For example, a test sample which includes the protein of interest is contacted with antibodies specific for a protein that is encoded by a gene having a mutation associated with glaucoma, as described above. Specific binding of the antibody to the protein of interest is indicative of a mutation associated with glaucoma.

The invention also pertains to methods of treating glaucoma, such as administration of a therapeutic agent that replaces, mimics or supplements the activity of the protein encoded by the gene associated with glaucoma, as well as methods of gene therapy for glaucoma.

The current invention facilitates identification of mutations in the genes which are associated with glaucoma, and thereby facilitates both better and earlier diagnosis and treatment of the disease. Identification of such mutations distinguishes one form of glaucoma from other forms, thereby enabling better treatment planning for affected individuals, as well as for other family members who may be affected individuals or disease carriers.

BRIEF DESCRIPTION OF THE FIGURES

FIG. 3 is a series of diagrams, individually labeled as FIG. 3A, FIG. 3B, and FIG. 3C, depicting the analysis of genomic mutations in five GLC3A families.

DETAILED DESCRIPTION OF THE INVENTION

Figure 1:
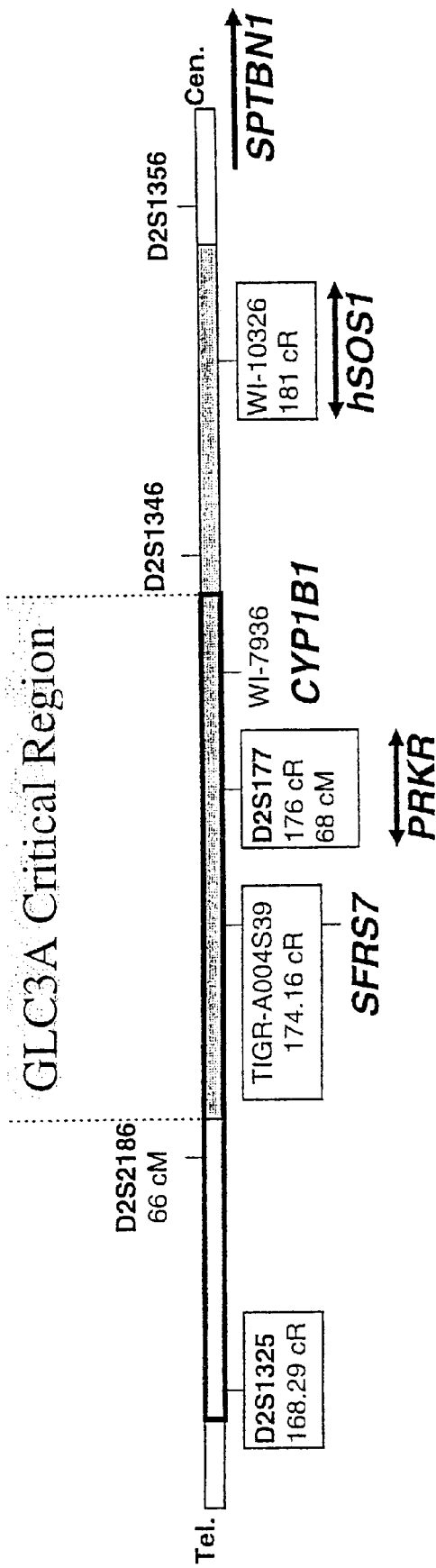
FIG. 1 is a depiction of the GLC3A critical candidate chromosomal region for genes associated with primary congenital glaucoma.

The current invention relates to methods of diagnosing glaucoma. The term "glaucoma", as used herein, refers to inherited glaucomas, such as primary congenital or infantile glaucoma; primary open angle glaucoma (POAG), including both juvenile-onset and adult- or late-onset POAG; secondary glaucomas; pigmentary glaucoma; and low tension glaucoma.

As described herein, Applicant has identified a gene associated with glaucoma: mutations in the gene are associated with the presence of disease. To identify the gene associated with glaucoma, Applicant investigated the genes that were present at a locus, GLC3A, that was linked with primary congenital glaucoma. After identifying candidate genes, Applicant performed direct sequencing analysis of the candidate genes from samples of genomic DNA from individuals in panels of families with primary congenital glaucoma. Applicant identified seventeen different mutations in the gene for human cytochrome P4501B1 (CYP1B1), as being associated with primary congenital glaucoma. One mutation, found in more than one family, was a 13 base pair deletion that removed nucleotides 1410 to 1422 (GAGTGCAGGCAGA (SEQ ID NO. 1)) from the coding sequence of the CYP1B1 gene. This mutation resulted in a frame shift that truncated the open reading frame by creating a premature stop codon 203 base pairs downstream of the deletions (68 amino acids after the last original (pre-frame shift) amino acid Thr-354). A second mutation in the CYP1B1 gene that was associated with primary congenital glaucoma was an insertion of an extra cytosine base in a stretch of six cytosines located between nucleotides 1209 to 1214. This insertion also resulted in a frame shift mutation that created a premature stop codon 106 base pairs downstream from the site of insertion (36 amino acids downstream from the last original amino acid Pro-289). A third type of mutation in the CYP1B1 gene also has a deletion that removes part of intron II and most of the coding sequence of exon III. A fourth mutation was a ten base pair duplication of nucleotides 1546–1555 (TCATGCCACC, SEQ ID NO. 20); this duplication of ten base pairs resulted in a frame shift mutation that created a premature stop after amino acid 403, removing 140 amino acids from the full-length (non-mutant) protein. A fifth mutation was a single base deletion of a cytosine at nucleotide 1737, resulting in a frame shift that created a premature stop codon TAG, resulting in the removal of 80 amino acids (a deletion of all amino acids after amino acid 463). A sixth mutation was a single base change (a G→T transition) at nucleotide 1187, which resulted in a premature TAA stop codon. A seventh mutation was a change in single base change (a C→T transition) at nucleotide 1482, which resulted in a change of the encoded amino acid from proline to leucine. An eighth mutation was a single base change (a G→C transition) at nucleotide 517, which resulted in a change of the encoded amino acid from tryptophan to cysteine. A ninth mutation was a single base change (a G→A transition) at nucleotide 528, which resulted in a change of the encoded amino acid from glycine to glutamic acid. A tenth mutation was an insertion of a thymine base at nucleotide 846, causing in a frame shift mutation that resulted in the deletion of 377 amino acids from the carboxy terminus of the protein. An eleventh mutation was a single base change (a G→T transition) at nucleotide 1439, which resulted in a change of the encoded amino acid from glycine to tryptophan. A twelveth mutation was a single base change (a G→A transition) at nucleotide 1505, resulting in a change of the encoded amino acid from glutamic acid to lysine. A thirteenth mutation was a single base change (a G→A transition) at nucleotide 1515, resulting in a change of the encoded amino acid from arginine to histidine. A fourteenth mutation was a single base change (a C→T transition) at nucleotide 1656, which resulted in a change of the encoded amino acid from proline to leucine. A fifteenth mutation was a deletion of a single base (G) at nucleotide 1691, causing a frame shift mutation that resulted in the deletion of 95 amino acids from the carboxy terminus of the protein. A sixteenth mutation was a single base change (a C→T transition) at nucleotide 1751, resulting in a change of the encoded amino acid from arginine to tryptophan. A seventeenth mutation was a duplication of 27 nucleotides beginning at nucleotide 1749 (i.e., duplication of nucleotides 1749–1775), causing a frame shift mutation that resulted in deletion of 76 amino acids from the carboxy terminus of the protein.

As a result of the discovery of these mutations in a gene associated with glaucoma, methods of diagnosing glaucoma are now available. Using methods such as those described herein, or other appropriate methods, it is now possible to identify genes associated with glaucoma. A "gene associated with glaucoma" is a gene that, if mutated, has a mutation that is associated with glaucoma. The "gene associated with glaucoma" includes the DNA encoding a protein, as well as other components, such as leader and trailer sequences, promoter elements, introns and exons. "Mutations associated with glaucoma", as described herein, include mutations in the gene as well as mutations in the cDNA or mRNA of the gene, wherein the mutations in the gene (or the cDNA or mRNA of the gene) have been determined to be associated with glaucoma, such as by linkage analysis (or by direct sequencing).

To identify other genes associated with glaucoma, analysis of loci known to be associated with glaucoma can be performed: genes within or closely linked to the locus of interest (the locus identified as being associated with glaucoma) can be analyzed for mutations, using methods such as those described below. For example, several loci have been assigned to adult-onset primary open angle glaucoma (POAG), including the 2cen-q13 region (Stoilova, D. et al., Genomics 26:142–150 (1996)); the 3q21-q22 region (Sarfarazi, M. et al., submitted 1996); 8q24 (Trifan, et al., in preparation); and 10p (Sarfarazi, M. et al., in preparation). These loci can be investigated to identify genes associated with glaucoma. Alternatively, new loci can be identified by genetic analysis of kindreds affected by glaucoma; these loci can then be analyzed to identify genes associated with glaucoma. These methods are applicable to all forms of glaucoma for which there is a genetic basis.

After identification of a gene associated with glaucoma, diagnosis is possible. Diagnosis of glaucoma is made by detecting a mutation or mutations in a gene associated with glaucoma. The mutation in the gene associated with glaucoma can be the insertion or deletion of a single nucleotide, or of more than one nucleotide, resulting in a frame shift mutation; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of the gene; duplication of all or a part of the gene; transposition of all or a part of the gene; or rearrangement of all or a part of the gene. More than one such mutation may be present in a single gene. Such sequence changes cause a mutation in the protein encoded by the gene associated with glaucoma. For example, if the mutation is a frame shift mutation, the frame shift can result in a change in the encoded amino acids, and/or can result in the generation of a premature stop codon, causing generation of a truncated protein. Alternatively, a mutation associated with glaucoma can be a synonymous mutation in one or more nucleotides (i.e., a mutation that does not result in a change in the protein encoded by the gene associated with glaucoma). Such a mutation may alter splicing sites, or otherwise affect the transcription or translation of the gene. A gene associated with glaucoma that has any of the mutations described above is referred to herein as a "mutant gene."

In a first method of diagnosing glaucoma, hybridization methods, such as Southern analysis, are used (see *Current Protocols in Molecular Bioloay*, Ausubel, F. et al., eds., John Wiley & Sons, including all supplements through 1997). For example, a test sample of genomic DNA, RNA, or cDNA, is obtained from an individual suspected of having (or carrying a defect for) glaucoma (the "test individual"). The individual can be an adult, child, or fetus. The test sample can be from any source which contains genomic DNA, such as a blood or tissue sample, such as from skin or other organs. In a preferred embodiment, the test sample of DNA is obtained from a fibroblast skin sample, from hair roots, or from cells obtained from the oral cavity (e.g., via mouthwash). In another preferred embodiment, the test sample of DNA is obtained from fetal cells or tissue by appropriate methods, such as by amniocentesis or chorionic villus sampling. The DNA, RNA, or cDNA sample is examined to determine whether a mutation associated with glaucoma is present; the presence of the mutation is indicated by hybridization of the gene in the genomic DNA, RNA, or cDNA to a nucleic acid probe. A "nucleic acid probe", as used herein, can be a DNA probe or an RNA probe. The nucleic acid probe hybridizes to at least one of the mutations associated with glaucoma, as described above. A fragment of such a nucleic acid probe can also be used, provided that the fragment hybridizes to the part of the gene that contains the mutation.

To diagnose glaucoma by hybridization, a hybridization sample is formed by contacting the test sample containing a gene associated with glaucoma, with at least one nucleic acid probe. The hybridization sample is maintained under conditions which are sufficient to allow specific hybridization of the nucleic acid probe to the gene associated with glaucoma. "Specific hybridization", as used herein, indicates exact hybridization (e.g., with no mismatches). Specific hybridization can be performed under high stringency conditions or moderate stringency conditions, for example. "Stringency conditions" for hybridization is a term of art which refers to the conditions of temperature and buffer concentration which permit hybridization of a particular nucleic acid to another nucleic acid in which the first nucleic acid may be perfectly complementary to the second, or the first and second nucleic acids may share only some degree of complementarity. For example, certain high stringency conditions can be used which distinguish perfectly complementary nucleic acids from those of less complementarity. "High stringency conditions" and "moderate stringency conditions" for nucleic acid hybridizations are explained in chapter 2.10 and 6.3, particularly on pages 2.10.1–2.10.16 and pages 6.3.1–6 in *Current Protocols in Molecular Biology*, supra, the teachings of which are hereby incorporated by reference. The exact conditions which determine the stringency of hybridization depend on factors such as length of nucleic acids, base composition, percent and distribution of mismatch between the hybridizing sequences, temperature, ionic strength, concentration of destabilizing agents, and other factors. Thus, high or moderate stringency conditions can be determined empirically. In one embodiment, the hybridization conditions for specific hybridization are moderate stringency. In a particularly preferred embodiment, the hybridization conditions for specific hybridization are high stringency.

Specific hybridization, if present, is then detected using standard methods. If specific hybridization occurs between the nucleic acid probe and the gene associated with glaucoma in the test sample, then the gene associated with glaucoma has a mutation. More than one nucleic acid probe can also be used concurrently in this method. Specific hybridization of any one of the nucleic acid probes is indicative of a mutation in the gene that is associated with glaucoma, and is therefore diagnostic for the disease.

For example, in the diagnosis of primary congenital glaucoma, a nucleic acid probe can be prepared that hybridizes to a part of the CYP1B1 gene having a 13 base pair deletion of nucleotides 1410 to 1422. If this nucleic acid probe specifically hybridizes with the gene associated with glaucoma in the test sample, a diagnosis of primary congenital glaucoma is made. Alternatively, a nucleic acid probe can be prepared that hybridizes to a CYP1B1 gene having one of the other mutations described above, such as: an extra cytosine (C) base located in the stretch of six cytosines between nucleotides 1209 and 1214; a 10 base pair duplication of nucleotides 1546–1555; a deletion of cytosine (C) at nucleotide 1737; a G→T transition at nucleotide 1187; a C→T transition at nucleotide 1482; a G→C transition at nucleotide 517; a G→A transition at nucleotide 528; an insertion of thymine (T) at nucleotide 846; a G→T transition at nucleotide 1439; a G→A transition at nucleotide 1505; a G→A transition at nucleotide 1515; a C→T transition at nucleotide 1656; a deletion of guanine (G) at nucleotide 1691; a C→T transition at nucleotide 1751; or a duplication of 27 nucleotides beginning with nucleotide 1749. Specific hybridization of such a nucleic acid probe with the gene associated with glaucoma in the test sample is indicative of primary congenital glaucoma.

In another hybridization method, Northern analysis (see *Current Protocols in Molecular Biology*, Ausubel, F. et al., eds., John Wiley & Sons, supra) is used to identify the presence of a mutation associated with glaucoma. For Northern analysis, a sample of RNA is obtained from the test individual by appropriate means. Specific hybridization of a nucleic acid probe, as described above, to RNA from the individual is indicative of a mutation in the gene that is associated with glaucoma, and is therefore diagnostic for the disease.

For representative examples of use of nucleic acid probes, see, for example, U.S. Pat. Nos. 5,288,611 and 4,851,330.

Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, Nielsen, P. E. et al., *Bioconjugate Chemistry*, 1994, 5, American Chemical Society, p. 1 (1994). The PNA probe can be designed to specifically hybridize to a gene having a mutation associated with glaucoma. Hybridization of the PNA probe to the mutant gene associated with glaucoma is diagnostic for the disease.

In another method of the invention, mutation analysis by restriction digestion can be used to detect mutant genes, if the mutation in the gene results in the creation or elimination of a restriction site. A test sample containing genomic DNA is obtained from the test individual. Polymerase chain reaction (PCR) can be used to amplify the gene associated with glaucoma (and, if necessary, the flanking sequences) in a test sample of genomic DNA from the test individual. RFLP analysis is conducted as described (see *Current Protocols in Molecular Biology*, supra). The digestion pattern of the relevant DNA fragment indicates the presence or absence of the mutation associated with glaucoma.

Sequence analysis can also be used to detect specific mutations in the gene. A test sample of DNA is obtained from the test individual. PCR can be used to amplify the gene, and/or its flanking sequences. The sequence of the gene associated with glaucoma, or a fragment of the gene, is determined, using standard methods. The sequence of the gene (or gene fragment) is compared with the known nucleic acid sequence of the gene. The presence of any of the mutations associated with glaucoma, as described above, indicates that the individual is affected with, or is a carrier for, glaucoma. In one embodiment of this method, such sequence analysis can be used to identify mutations in the CYP1B1 gene that are associated with glaucoma.

Allele-specific oligonucleotides can also be used to detect the presence of a mutation associated with glaucoma, through the use of dot-blot hybridization of amplified gene products with allele-specific oligonucleotide (ASO) probes (see, for example, Saiki, R. et al., (1986), *Nature* (London) 324:163–166). An "allele-specific oligonucleotide" (also referred to herein as an "allele-specific oligonucleotide probe") is an oligonucleotide of approximately 10–50 base pairs, preferably approximately 15–30 base pairs, that specifically hybridizes to the gene that contains a mutation associated with glaucoma. An allele-specific oligonucleotide probe that is specific for particular mutations in the gene associated with glaucoma can be prepared, using standard methods (see *Current Protocols in Molecular Bioloay*, supra). To identify mutations in the gene that are associated with glaucoma, a test sample of DNA is obtained from the test individual. PCR can be used to amplify all or a fragment of the gene associated with glaucoma, and its flanking sequences. The DNA containing the amplified gene associated with glaucoma (or fragment of the gene) is dot-blotted, using standard methods (see *Current Protocols in Molecular Biology*, supra), and the blot is contacted with the oligonucleotide probe. The presence of specific hybridization of the probe to the amplified gene associated with glaucoma is then detected. Specific hybridization of an allele-specific oligonucleotide probe to DNA from the individual is indicative of a mutation in the gene associated with glaucoma that is associated with glaucoma, and is therefore diagnostic for the disease.

Diagnosis of glaucoma can also be made by examining expression of the protein encoded by the gene associated with glaucoma. A test sample from an individual is assessed for the presence of an alteration in the expression of the gene associated with glaucoma. An alteration in expression of a protein encoded by a gene associated with glaucoma can be an alteration in the quantitative protein expression (i.e., the amount of protein produced); an alteration in the qualitative protein expression (i.e., the composition of the protein), or both. An "alteration" in the protein expression, as used herein, refers to an alteration is a test sample as compared with the expression of protein by a gene associated with glaucoma in a control sample. A control sample is a sample that corresponds to the test sample (e.g., is from the same type of cells), and is from an individual who is not affected by glaucoma. An alteration in the expression of the protein in the test sample, as compared with the control sample, is indicative of glaucoma. Various means of examining expression of protein encoded by the gene associated with glaucoma can be used, including spectroscopy, colorimetry, electrophoresis, isoelectric focusing, and immunoblotting (see *Current Protocols in Molecular Biology*, particularly chapter 10). For example, Western blotting analysis, using an antibody that specifically binds to a protein encoded by a mutant gene, or an antibody that specifically binds to a protein encoded by a non-mutant gene, can be used to identify the presence in a test sample of a protein encoded by a mutant gene associated with glaucoma, or the absence in a test sample of a protein encoded by a non-mutant gene. The presence of a protein encoded by a mutant gene, or the absence of a protein encoded by a non-mutant gene, is diagnostic for glaucoma.

In one embodiment of this method, the level or amount of protein encoded by a gene associated with glaucoma in a test sample is compared with the level or amount of the protein encoded by the gene associated with glaucoma in a control sample. A level or amount of the protein in the test sample that is higher or lower than the level or amount of the protein in the control sample, such that the difference is statistically significant, is indicative of an alteration in the expression of the protein encoded by the gene associated with glaucoma, that is associated with disease. Alternatively, the composition of the protein encoded by a gene associated with glaucoma in a test sample is compared with the composition of the protein encoded by the gene associated with glaucoma in a control sample. A difference in the composition of the protein in the test sample, as compared with the composition of the protein in the control sample, is indicative of glaucoma. In another embodiment, both the level or amount and the composition of the protein can be assessed in the test sample and in the control sample. A difference in the amount or level of the protein in the test sample, compared to the control sample; a difference in composition in the test sample, compared to the control sample; or both a difference in the amount or level, and a difference in the composition, is indicative of disease.

The invention also relates to antibodies to mutant proteins encoded by genes associated with glaucoma. A "mutant protein", as referred to herein, is a protein or protein fragment that is encoded by a mutant gene associated with glaucoma. Once a mutation in a gene associated with glaucoma has been identified, the protein or protein fragment encoded by the mutated gene (also referred to herein as the protein of interest) can be identified, and antibodies can be raised to the protein or protein fragment using standard methods (see, for example, *Current Protocols in Molecular Biology*, supra). The term "antibody", as used herein, encompasses both polyclonal and monoclonal antibodies, as well as mixtures of more than one antibody reactive with the protein or protein fragment (e.g., a cocktail of different types of monoclonal antibodies reactive with the mutant protein or protein fragment). The term antibody is further intended to encompass whole antibodies and/or biologically functional fragments thereof, chimeric antibodies comprising portions from more than one species, humanized antibodies, human-like antibodies, and bifunctional antibodies. Biologically functional antibody fragments are those fragments sufficient for binding of the antibody fragment to the protein of interest.

Monoclonal antibodies (mAb) reactive with a mutant protein encoded by a gene associated with glaucoma can be produced using somatic cell hybridization techniques (Kohler and Milstein, *Nature* 256:495–497 (1975)) or other techniques. In a typical hybridization procedure, a crude or purified mutant protein encoded by a gene associated with glaucoma can be used as the immunogen. An animal is immunized with the immunogen to obtain antibody-producing spleen cells. The species of animal immunized will vary depending on the specificity of mAb desired. The antibody producing cell is fused with an immortalizing cell (e.g., a myeloma cell) to create a hybridoma capable of secreting antibodies to the mutant protein of the invention. The unfused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal in a similar fashion as described above for the production of monoclonal antibodies. The animal is maintained under conditions whereby antibodies are produced that are reactive with the mutant protein encoded by the gene associated with glaucoma. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG, IgM).

Antibodies that specifically bind to a protein or protein fragment encoded by the mutant gene associated with glaucoma (i.e., those that bind to the protein or protein fragment encoded by the mutant gene, but not to protein encoded by a non-mutant copy of the gene) can also be used in methods of diagnosis. A test sample containing the protein encoded by the gene associated with glaucoma is contacted with the antibody; binding of the antibody to the protein is indicative of the presence of a protein encoded by the mutant gene, and is diagnostic for disease.

The present invention also includes kits useful in the methods of the invention. The kits can include a means for obtaining a test sample; nucleic acid probes, PNA probes, or allele-specific oligonucleotide probes; appropriate reagents; antibodies to mutant proteins encoded by genes associated with glaucoma; instructions for performing the methods of the invention; control samples; and/or other components.

The invention also pertains to modes of therapy to treat glaucoma. Glaucoma can be treated by administration of an agent that, when administered, ameliorates, relieves, lessens the severity of, or eliminates the symptoms of glaucoma. For example, an antibody that specifically binds to the mutant protein encoded by the gene associated with glaucoma can be administered, in order to reduce or eliminate activity by the mutant protein. Alternatively or in addition, the non-mutant protein encoded by the gene associated with glaucoma can be administered as a therapeutic agent to treat glaucoma. In another embodiment, an agent that mimics the activity of the protein encoded by the gene associated with glaucoma (the mutant protein) can be administered, in order to supplement or supplant the activity of a protein encoded by the mutant gene associated with glaucoma. For example, peptides which have the same biological activity as the protein encoded by the gene associated with glaucoma can be used. Peptidomimetics (molecules which are not polypeptides, but which mimic aspects of their structures) can be also designed based on the structure of the protein encoded by the gene associated with glaucoma. Polysaccharides can be prepared that have the same functional groups as the protein, and which have the same function as the protein. Alternatively, libraries of agents, such as those that can be constructed using well-known methods of combinatorial chemistry, can be assayed for additional agents. Such agents can be isolated by standard methods, such as by interaction of the agent with an antibody that also specifically binds to the protein encoded by the gene associated with glaucoma.

In another embodiment, an agent that induces or enhances expression of a related gene, such that expression of the protein encoded by the related gene supplements or supplants activity of the mutant protein, can be used. Replacement or supplementation of the activity of the mutant protein will reduce or eliminate the physiological cause of glaucoma, and thereby treat the disease. Such agents can include proteins, peptides, peptidomimetics, antibodies, or other small molecules that induce or enhance expression of a related gene. For example, an agent that induces or enhances expression of another protein in the cytochrome p450 family can be used to treat congenital glaucoma, by supplementing or replacing the activity of a mutant CYP1B1 gene. Alternatively, an DNA construct that induces or enhances expression of a related gene can be generated, such as by the methods described in WO 95/31560, for example.

Alternatively or in addition, an antibody that specifically binds to the mutant protein encoded by the gene associated with glaucoma can be administered before, after, or concurrently with any of the agents described above, in order to target the mutant protein and reduce or eliminate its activity.

Glaucoma can also be treated by the administration of genes, gene transfer vectors, or other nucleic acid constructs. A non-mutant copy of the gene (or cDNA of the gene) associated with glaucoma, or mRNA of a non-mutant copy of the gene (or cDNA) associated with glaucoma, can be provided to the individual. For example, a gene transfer vector containing a non-mutant gene associated with glaucoma can be administered, to express the non-mutant gene in the individual affected by glaucoma. The gene transfer vector can also contain tissue-specific promoters, as well as other elements (e.g., enhancer elements, splicing signals, termination and polyadenylation signals, viral replicons, bacterial plasmid sequences, or other vector nucleic acid sequences). Delivery of the vector can be targeted to particular regions or cell types (e.g., by the use of decorated liposomes, or by introducing the vector in a specific region of the body). Alternatively, purified DNA or mRNA can be used as a therapeutic agent, as described in WO 93/19183 or in WO 90/11092. These methods can also be used to introduce a related gene, such that expression of the protein encoded by the related gene supplements or supplants activity of the mutant protein.

In another embodiment, a nucleic acid construct that targets the mutant gene associated with glaucoma, and "corrects" the mutation by integration or by homologous recombination, can be used. Constructs that use homologous recombination to provide DNA encoding a therapeutic protein or peptide are described in WO 93/09222, for example. Gene therapy as described above can target cells in vivo, by administration of the therapeutic agent directly to the individual. Alternatively, the gene therapy can target cells in vitro, such as cells that have been removed from the individual; the treated cells can then be reimplanted into the individual. The entire teachings of the publications cited in the above paragraph are incorporated herein by reference.

Therapeutic agents, including the agents described above as well as the gene transfer vectors, DNA, and/or mRNA described above in relation to gene therapy, can be administered opthamologically, subcutaneously, intravenously, intramuscularly, topically, orally, rectally, vaginally, nasally, buccally, by inhalation spray, or via an implanted reservoir. In a preferred embodiment, the therapeutic agent is administered to the eye, such as by topical administration (e.g., eye drops or emulsion). They can be administered in dosage formulations containing conventional non-toxic pharmaceutically-acceptable carriers, adjuvants and/or vehicles. The form in which the agents are administered (e.g., capsule, tablet, solution, emulsion) will depend at least in part on the route by which they are administered. A therapeutically effective amount of the agent is that amount necessary to significantly reduce or eliminate symptoms associated with glaucoma. The therapeutically effective amount will be determined on an individual basis and will be based, at least in part, on consideration of the agent, the individual's size and gender, the severity of symptoms to be treated, the result sought. Thus, the therapeutically effective amount can be determined by one or ordinary skill in the art, employing such factors and routine experimentation.

The therapeutically effective amount can be administered in a series of doses separated by appropriate intervals, such as hours, days or weeks. Alternatively, the therapeutically effective amount can be administered in a single dose. The term, "single dose," as used herein, can be a solitary dose, and can also be a sustained release dose, such as by a controlled-release dosage formulation of a continuous infusion. Other drugs can also be administered in conjunction with the agent.

The invention is further illustrated by the following Example.

EXAMPLE

Identification of a Gene Associated with Glaucoma Screening Panel and Identification of Loci A screening panel of 17 families with primary congenital glaucoma was used (Sarfarazi, M. et al., Genomics 30:171 (1995); Turacli, M. E. et al., Int. Ophthamol. 16:359 (1992)). After excluding many genes and candidate chromosomal regions (Akarsu, A. N. et al., Am. J. Med. Genet 61:290 (1996); Akarsu, A. N. et al., Am. J. Med. Genet. 62:102 (1996)), a random screening of the genome assigned two loci, GLC3A (2p21, Sarfarazi, M. et al., Genomics 30:171 (1995)) and GLC3B (1p36, Akarsu, A. N. et al., Hum. Mol. Genetics 5:1199 (1996)) for primary congenital glaucoma, with evidence for at least one additional unmapped locus for the condition. The GLC3A locus on 2p21 has recently been confirmed in another panel of 25 families from Saudi Arabia (Bejjani, B. A. et al., Am. J. Human Genet. 59 suppl., A212–1216 (1996)). Two additional families are also identified. therefore, the GLC3A locus emerges as a major location for this condition, with nearly 85% of the tested families being linked to this site.

Critical recombination events and inspection of the smallest conserved segment of homozygosity in the affected members of consanguineous families (Sarfarazi, M. et al., Genomics 30:171 (1995)) reduced the GLC3A critical candidate region to approximately 2.5 cM that is flanked by markers D2S2186 and D2S1346. This candidate region is shown in FIG. 1. The directions toward the centromere and telomere are indicated. Loci anchored on the Chromosome 2 Radiation Hybrid map (Hudson, T. et al., *Science* 270:1945 (1995)) are boxed. The distances (in cR or cM) from top of Chromosome 2 are indicated. The area shaded in gray represents the GLC3A candidate region as defined by recombination events with markers D2S2186 (Bejjani, B. A. et al., *Am. J. Hum. Genet.* 59 suppl:A212/1216 (1996)) and D2S1356 (Sarfarazi, M. et al., *Genomics* 30:171 (1995)). The dark edged box identifies the smallest segment of homozygosity observed in our consanguineous families. Black horizontal arrows represent the interval within which a particular gene is mapped.

Three genes have been previously mapped to the 2p21 region: non-erythrocytic form of beta-spectrin or beta-fodrin (SPTBN1) (Chang, J. G. et al., *Genomics* 17:287 (1993); Hu, R. J. et al., *J. Biol. Chem.* 267:18715 (1992)); a guanine nucleotide exchange factor for Ras (hSOS1) (Chardin, P. et al., *Science* 260:1338 (1993)); Webb, G. C. et al., *Genomics* 18:14 (1993)); and interferon-inducible dsRNA-dependent protein kinase (PRKR) (Barber, G. N. et al., *Genomics* 16:765 (1993); Squire, J. et al., *ibid* 16:768 (1993); Hanash, S. M. et al., *Genes Chromosom Cancer* 8:34 (1993)). These genes were implicated as possible candidate genes for this conditions. The positions of the genes were refined by screening them against the GeneBridge 4 Radiation Hybrid (RH) panel and mapping them relative to the Whitehead Rh framework (Hudson, T. et al., *Science* 270:1945 (1995)). The original MIT order of 91 cell lines was used. Statistical analysis of the RH data was carried out on the mapping server at Whitehead Institute for Genome Research. Detailed RH map information can be obtained from http://www-genome.wi.mit.edu. Screening of the RH panel was carried out by gene specific polymerase chain reaction (PCR) assays. Preferably, the intronic or 3-prime untranslated sequences were assayed to prevent cross-amplification of the hamster DNA background. Map positions for these genes were established as follows (see FIG. 1): SPTBN1 mapped 1.51 centiRay (cR) from marker WI-4077 (LOD >3.0); hSOS1 positioned 1.51 cR from marker WI-10326 (LOD >3.0); and PRKR was placed 2.3 cR from D2S177 (LOD >3). therefore, SPTBN1 maps centromerically to D2S1356 and thus was excluded as a candidate gene for GLC3A.

Inspection of the contig map (Hudson, T. et al., *Science* 270:1945 (1995); Shuler, G. D. et al, *Science* 274:540 (1996)) harboring the GLC3A locus revealed that marker WI-7936 maps very closely to D2S177. this sequence tagged site (STS) corresponds to the gene for human cytochrome P4501B1 (CYP1B1) (Sutter, T. R. et al., *J. Biol. Chem.* 269:13092 (1994)). A fifth gene encoding 9G8 splicing factor (SFRS7) was identified when a BLAST search determined that the expressed sequence tagged (EST) marker TIGR-A004S39 has been derived from the 3-prime untranslated region of this gene (Popielarz, M. et al., *J. Biol. Chem.* 270:17830 (1995)). This EST has already been mapped next to marker D2S177 on the chromosome 2 RH map (Hudson, T. et al., *Science* 270:1945 (1995); Shuler, G. D. et al, *Science* 274:540 (1996)). All of these genes were considered as potential candidate genes; coding sequences of several of the genes were screened for mutations by a direct sequencing method.

Monolayers of human skin fibroblasts were maintained at 37° C. in a $CO_2$ incubator, in media MEM (Gibco/BRL, catalog number 11095-080) supplemented with 10% Fetal Bovine Serum and antibiotics (penicillin G, streptomycin sulfate; Gibco/BRL catalog number 15140-015). Total RNA was prepared with TRIzol reagent (Gibco/BRL) according to manufacturer's protocols. First strand synthesis was primed from 10 µl of the RNA sample with 50 ng random hexamers. Reaction was carried out in 20 mM Tris-HCl (pH 8.4), 40 mM KCl, 2.5 mM $MgCl_2$, 0.5 mM from each dNTP, 0.01 M DDT, and 200 U SuperScript II RT (Gibco) in a total volume of 20 µl for 1 hour at 42° C. The coding sequence of the CYP1B1 gene was amplified with the cDNA-based primer sets:
CYP1 (CYP1F 5'-GGTTCCTGTTGACGTCTTG-3' (SEQ ID NO. 2), CYP1R 5'-CTTCCAGTGCTCCGAGTAG-3' (SEQ ID NO. 3));
CYP2 (CYP2F 5'-GTGGTGCTGAATGGCGAG-3' (SEQ ID NO. 4), CYP2R 5'-TACTGCAGCCAGGGCATC-3' (SEQ ID NO. 5));
CYP3 (CYP3F 5'-GTGGCCAACGTCATGAGTG-3' (SEQ ID NO. 6), CYP3R 5'-TCATAAAGGAAGGCCAGGAC-3' (SEQ ID NO. 7);
and CYP4 (CYP4F 5'-AGACTCGAGTGCAGGCAG-3' (SEQ ID NO. 8), CYP4R 5'-TCCTCATCTCCGAAGATGGT-3' (SEQ ID NO. 9)). PCR amplification was carried out with recombinant Taq polymerase (Gibco/BRL) according to the manufacturer's protocol. The amplified PCR fragments were purified directly or from agarose gels with Wizard PCR preps DNA purification system (Promega). Dye terminator sequencing with Taq Polymerase FS was performed on an ABI-373 sequencer (Perkin Elmer).

Initially, the coding sequences of the hSOS1 and PRKR genes were screened; when no sequence variants were observed, mutation screening of the CYP1B1 gene was performed.

As a result of this screening, a 13 bp homozygous deletion (family 26; affected individual 10) that removed nucleotides 1410 to 1422 (i.e., GAGTGCAGGCAGA (SEQ ID NO. 1)) from the coding sequences (i.e., exon III) of the CYP1B1 gene was identified. This mutation resulted in a frameshift that truncated the open reading frame by creating a premature stop codon (TGA), 203 bp downstream of this deletion (or 68 amino acids after the last original amino acid Thr-354). In order to develop an assay for genomic DNA screening, the intron/exon junctions of this gene were determined. In order to recover the genomic region containing the CYP1B1 coding sequence, the cDNA-based primer sets CYP1–4 were used for long-range PCR amplification. Total yeast DNA prepared from strain containing YAC 806-F-8 (Hudson, T. et al., *Science* 270:1945 (1995)) served as a template. Approximately 50 ng total yeast DNA were subjected to PCR amplification with 20 pmol of each primer in a total volume of 50 µl that consisted of 60 mM $Tris-SO_4$ (pH 9.1 at 25° C.), 18 mM $(NH_4)_2SO_4$, 1.5 mM $MgSO_4$, 0.2 mM each dNTP, and 2 µl eLONGase enzyme mix (Gibco/BRL). Amplification conditions consisted of 1 min initial denaturation at 94° C., followed by 35 cycles of denaturation at 94° C. for 30 seconds, annealing at 53° C. for 30 seconds, and 6 minute extension at 68° C. As a result, four PCR fragments ranging in size from 1 kb to 3 kb were amplified. Purification and sequencing of these fragments were performed as described above. Intron/exon junctions in the CYP1B1 gene were identified by comparing the sequences of the amplified fragments to the reference cDNA sequence (Sutter, T. R. et al., *J. Biol. Chem.* 269:13092 (1994)). Three primer sets were assembled for amplification of the CYP1B1 coding sequence from genomic DNA. Primer CYP1F was paired with the intronic primer, 5'-CCTCCCAGAGGCTTTACCT-3' (SEQ ID NO. 10), for amplification of exon II under the conditions described for the long distance PCR (1.6 kb fragment). For amplification of the coding region located in exon III, intronic primer 5'-TAAGAATTTTGCTCACTTGC-3' (SEQ ID NO. 11) was paired with primer CYP4R (693 bp fragment). A 134 bp fragment containing the 3'-end of the CYP1B1 coding sequence was amplified with primers 5'-TCAATGTCACTCTCAGAGAG-3' (SEQ ID NO. 12) and CYP4R. It was concluded that the CYP1B1 gene contains three exons and two introns, as shown in Table 1.

TABLE 1

Exons in CYP1B1 Gene

| Exon No. | Exon Size | Intron Location | 5' Splice Donor | 3' Splice Acceptor |
|---|---|---|---|---|
| I | 345 | 345/346 | CGCAGgtcagt (SEQ ID NO. 13) | cccagCATGG (SEQ ID NO. 14) |
| II | 1044 | 1389/1390 | ACCAGgtaaag (SEQ ID NO. 15) | aacagGTATC (SEQ ID NO. 16) |
| III | 3703* | | | |

*3121 bp 3'-untranslated sequence

Figure 2:
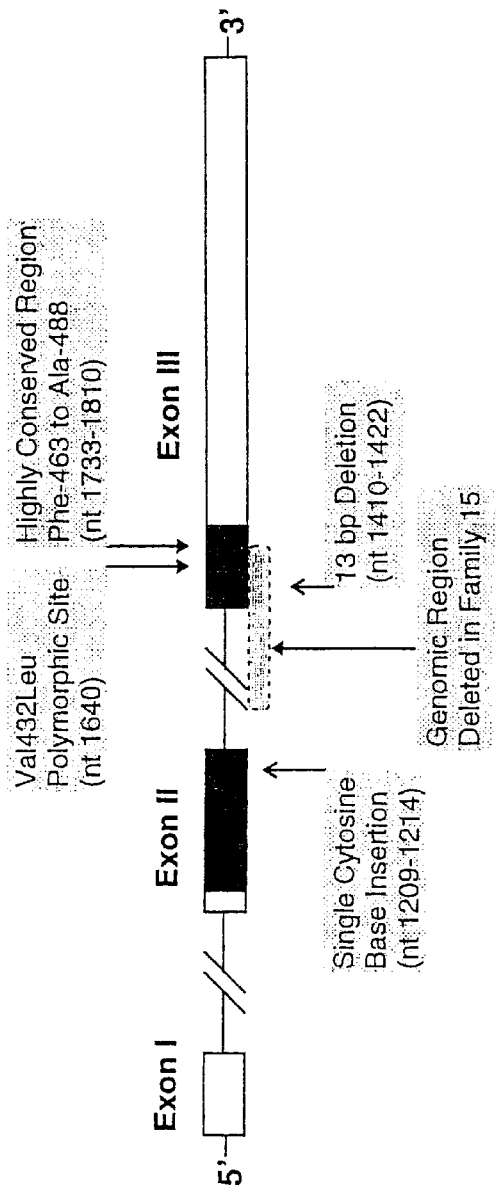
FIG. 2 is a depiction of the genomic structure of the CYP1B1 gene, with three mutations associated with glaucoma identified.

The genomic structure of the gene is shown in FIG. 2. The numeration reflects the cDNA sequence of the gene, and the coding regions are shown in black. The entire coding sequence of the gene is contained in exons two and three.

The genomic structure of CYP1B1 determined here is in agreement with the result published recently (Tang, Y. M. et al., *J. Biol. Chem.* 271:28324 (1996)).

Figure 3A:
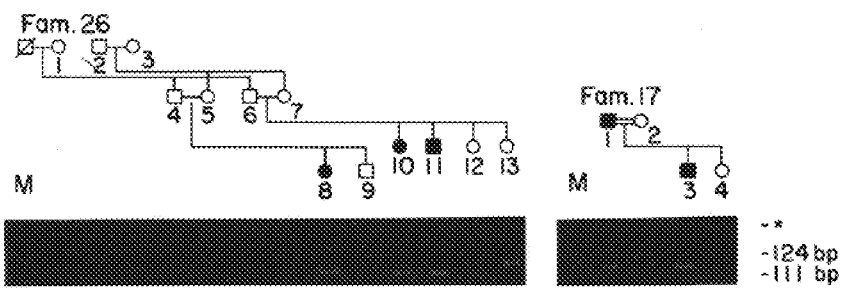
FIG. 3A depicts a 13 base pair deletion in families 17 and 26 as assayed by acrylamide gel electrophoresis and sequencing.

The presence of the 13 bp exonic deletion in family 26 and its cosegregation with the disease phenotype was confirmed by acrylamide gel electrophoresis of a 124 bp PCR fragment that harbored the deleted region. For rapid mutation screening, a 124 bp fragment containing the 13 bp deletion was amplified from genomic DNA with primers: 5'-CAAACAGGTATCCTGATGTG-3' (SEQ ID NO. 17) and CYP3R. The PCR products were analyzed on polyacrylamide minigels consisting of 5% Acrylamide/Bis solution (19:1), 15% urea, and 1× TBE (see FIG. 3A). The same 13 bp deletion was also detected and subsequently confirmed to segregate with the disease phenotype in another family (family 17; FIG. 3A). The third band (*) observed in the heterozygote individuals represents a heteroduplex. Family 17 is a consanguineous marriage between an affected father and a normal mother. In this pedigree, it was determined that the father is homozygote for the 13 bp deletion while the mother is heterozygote for the same deletion. Therefore, all the affected and normal offspring have inherited a single copy of this deletion from his father alone, while the affected offspring, in addition, inherited a 13 bp deletion from his mother.

Figure 3B:
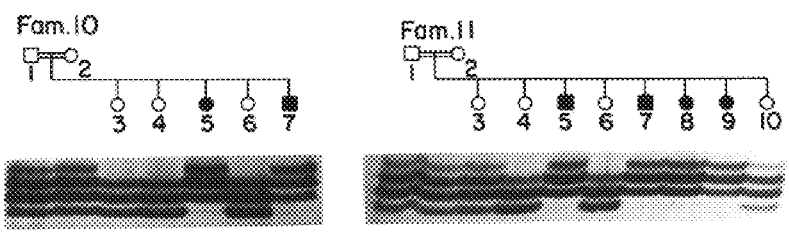
FIG. 3B depicts analysis of the single cytosine base insertion in families 10 and 11.

A second mutation was observed by rapid mutation screening as described above, in another two families (families 10 and 11) who exhibited a homozygous insertion of an extra cytosine base in a stretch of six cytosines located between nucleotide positions of 1209 to 1214 in exon II (FIGS. 2 and 3B). This also proved to be a frameshift mutation that created a premature stop codon (TGA), 106 bp downstream from the site of this insertion (or 36 amino acids downstream from the original amino acid Pro-289).

Figure 3C:
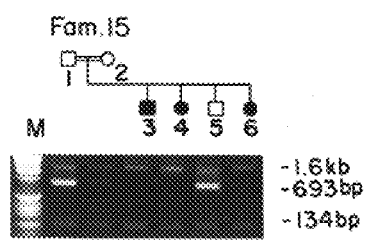
FIG. 3C depicts PCR characterization of a large deletion observed in family 15.

Furthermore, a third mutation was detected in another consanguineous family (family 15). This is a much larger deletion that starts in intron II and removes a certain portion of coding sequences of exon III that extends beyond the above-mentioned 13 bp deletion (FIGS. 2, 3C). An assay for rapid mutation screening as described above was used. The mutation detected in exon II was amplified from genomic DNA with primers: 5'-GACAAGTTCTTGAGGCACTGC-3' (SEQ ID NO. 18) and 5'-ACGTTCTCCAAATCCAGCC-3' (SEQ ID NO. 19) The amplified fragments were electrophoresed on sequencing type acrylamide gel under denaturing conditions (1 M urea, 50–54° C.). Gels were visualized by silver staining. From the PCR amplification pattern, it is shown that the 5-prime end of exon III and the adjacent intronic region are deleted, but that the 3-prime end of exon III has remained intact (FIG. 3C). The top band represents a 1.6 kb fragment containing the entire exon II and the adjacent 5-prime intron. The second fragment contains the entire coding sequence located in exon III. The smallest amplification product contains 134 bp from the 3'-end of the CYP1B1 coding sequence. As the 3-prime splice acceptor site of intron II has been deleted, this mutation is expected to interfere with the normal splicing of the CYP1B1 gene, resulting in synthesis of either truncated protein, or null allele.

A fourth mutation was detected in an individual. This mutation is a 10 base pair duplication of nucleotides 1546–1555 (TCATGCCACC, SEQ ID NO. 20), which results in a frame shift mutation that created a premature stop codon. The premature stop codon resulted in a deletion of all amino acits after amino acid 403 (deletion of the last 140 amino acids).

Analysis of 470 chromosomes from randomly selected normal individuals (330 Turkish and 140 other Caucasians) failed to detect the presence of the four mutant alleles described above, making it less likely that these sequence variants represent rare polymorphism. These mutations were only observed in 18 affected subjects but not the normal members of a total of 7 families (including 5 consanguineous families), and, the normal population from which these families are ascertained did not carry these mutations, strongly suggesting that the CYP1B1 gene is the gene for the GLC3A locus on 2p21.

A fifth mutation was a single base deletion of cytosine at nucleotide 1737. This mutation similarly resulted in a frame shift mutation that created a premature stop codon. The premature stop codon resulted in the deletion of 80 amino acids (all amino acids after amino acid 463).

A sixth mutation was a single base, G→T transition of nucleotide 1188. This mutation created a premature TAA stop codon after amino acid 281, removing 263 amino acids from the full-length protein.

A single base pair C→T transition at nucleotide 1482 was also detected. This change results in a change of the encoded amino acid from proline to leucine.

Ten additional mutations have also been identified. These mutations were either sporadic or familial, and found in one or more individuals or families from varying geographical populations (families of Turkish, US, Pakistani, UK, Hispanic or French Canadian origin). The following mutations were found: a single base change (a G→C transition) at nucleotide 517, resulting in a change of the encoded amino acid from tryptophan to cysteine; a single base change (a G→A transition) at nucleotide 528, resulting in a change of the encoded amino acid from glycine to glutamic acid; an insertion of a thymine base at nucleotide 846, causing a frame shift mutation that resulted in the deletion of 377 amino acids from the carboxy terminus of the protein; a single base change (a G→T transition) at nucleotide 1439, resulting in a change of the encoded amino acid from glycine to tryptophan; a single base change (a G→A transition) at nucleotide 1505, resulting in a change of the encoded amino acid from glutamic acid to lysine; a single base change (a G→A transition) at nucleotide 1515, resulting in a change of the encoded amino acid from arginine to histidine; a single base change (a C→T transition) at nucleotide 1656, resulting in a change of the encoded amino acid from proline to leucine; a deletion of a single base (G) at nucleotide 1691, causing a frame shift mutation that resulted in the deletion of 95 amino acids from the carboxy terminus of the protein; a single base change (a C→T transition) at nucleotide 1751, resulting in a change of the encoded amino acid from arginine to tryptophan; or a duplication of 27 nucleotides, beginning at nucleotide 1749, causing a frame shift mutation that resulted in deletion of 76 amino acids from the carboxy terminus of the protein.

The mutations described above are summarized in Table 2. The "location in protein" in Table 2 indicates the region of the protein's structure having the mutation; and the "restriction sites" indicates the addition or deletion of restriction sites. The changes in the restriction sites can be used, for example, to perform mutation analysis by restriction digestion, as described above. The first five mutations are within exon II; the remaining mutations affect exon III.

TABLE 2

Mutations Associated with Primary Congenital Glaucoma

| Position** | DNA change | Effect of change | Location in protein | COOH— Amino acids deleted | Restriction sites |
|---|---|---|---|---|---|
| 517 | G--->C | Trp(57)--->Cys | hinge region | n/a | n/a |
| 528 | G--->A | Gly(61)--->Glu | hinge region | n/a | + TaqI |
| 846 | insert T | frameshift | n/a | 377 | − XhoI |
| 1187 | G--->T | Glu(281)--->stop | n/a | 262 | n/a |
| 1209 | insert C | frameshift | n/a | 254 | n/a |
| exon II, III | large deletion | splicing error | n/a | n/a | n/a |
| 1410 | delete 13 nucleotides | frameshift | n/a | 189 | − XhoI |
| 1439 | G--->T | Gly(365)--->Trp | J-helix | n/a | n/a |
| 1482 | C--->T | Pro(379)--->Leu | K-helix | n/a | n/a |
| 1505 | G--->A | Glu(387)--->Lys | K-helix | n/a | n/a |
| 1515 | G--->A | Arg(390)--->His | K-helix | n/a | − CfoI |
| 1546 | duplicate 10 aa | frameshift | n/a | 140 | + NIa III |
| 1656 | C--->T | Pro(437)--->Leu | Meander | n/a | n/a |
| 1691 | G deletion | frameshift | n/a | 95 | n/a |
| 1751 | C--->T | Arg(469)--->Trp | Heme-binding | n/a | − AciI |
| 1749 | duplicate 27 aa | frameshift | n/a | 76 | + BlaI |
| 1737 | C deletion | stop codon | n/a | 80 | n/a |

**The position is the nucleotide that is altered, inserted or deleted, or the nucleotide at which a duplication begins, unless otherwise indicated.

If a stable protein product is produced from the mutated genes described above, the products are expected to lack from 80 to 377 amino acids from the —COOH terminus. This segment harbors the invariant cysteine of all known cytochrome P450 amino acid sequences (i.e., Cys-470 of CYP1B1). This residue provides the axial heme ligand that defines many of the functional and spectral characteristics of the cytochrome P450 proteins (Hudson, T. et al., *Science* 270:1945 (1995); Gonzalez, F. J., *Pharmacol. Rev.* 40:243 (1989))). The adjacent residues Phe-463 to Gly-472, correspond to the protein sequence pattern that identifies the cysteine heme-iron ligand signature sequence of cytochrome P450 (PROSITE accession PS00086; (Hudson, T. et al., *Science* 270:1945 (1995); Bairoch, A., *Nucl. Acids Res.* 20 (suppl) :2013 (1992)). The removal of this essential region is expected to interfere with the ability of the truncated molecules to perform normal physiologic functions.

A G to C transversion at nucleotide 1640 of the CYP1B1 coding sequence, which changes Val-432 to Leu, has also been detected (FIG. 2). This change was found to create and Eco57I restriction site, thus providing a rapid screening method. A total of 70 normal individuals (47 Turkish and 23 other Caucasians) were screened for the presence or absence of this change. Thirty-six individuals (51.4%) were found to be heterozygote for this change. Of the remaining 34 homozygote individuals (48.6%), 27 subjects had leucine and 7 had valine. The amino acid position where this change has occurred is not part of the CYP1B1 conserved sequence; further, both valine and leucine are neutral and hydrophobic amino acids with similar aliphatic side groups differing only by a single $CH_2$ group. Thus, this change represents a polymorphism that is unrelated to the primary congenital glaucoma phenotype.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of diagnosing primary congenital glaucoma in an individual, comprising detecting a deletion of nucleotide 1691 in the human cytochrome P4501B1 gene, wherein the presence of the deletion is indicative of primary congenital glaucoma.

2. A method of diagnosing primary congenital glaucoma in an individual, comprising detecting an insertion of a single thymine residue at nucleotide 846 in the human cytochrome P4501B1 gene, wherein the presence of the insertion is indicative of primary congenital glaucoma.

3. A method of diagnosing primary congenital glaucoma in an individual, comprising detecting a duplication of nucleotides 1749–1775 in the human cytochrome P4501B1 gene, wherein the presence of the duplication is indicative of primary congenital glaucoma.

4. A method of diagnosing primary congenital glaucoma in an individual, comprising detecting a change of nucleotide 517 from G to C in the human cytochrome P4501B1 gene, wherein the presence of the insertion is indicative of primary congenital glaucoma.

5. A method of diagnosing primary congenital glaucoma in an individual, comprising detecting a change of nucleotide 528 from G to A in the human cytochrome P4501B1 gene, wherein the presence of the insertion is indicative of primary congenital glaucoma.

6. A method of diagnosing primary congenital glaucoma in an individual, comprising detecting a change of nucleotide 1439 from G to T in the human cytochrome P4501B1 gene, wherein the presence of the insertion is indicative of primary congenital glaucoma.

7. A method of diagnosing primary congenital glaucoma in an individual, comprising detecting a change of nucleotide 1505 from G to A in the human cytochrome P4501B1 gene, wherein the presence of the insertion is indicative of primary congenital glaucoma.

8. A method of diagnosing primary congenital glaucoma in an individual, comprising detecting a change of nucleotide 1515 from G to A in the human cytochrome P4501B1 gene, wherein the presence of the insertion is indicative of primary congenital glaucoma.

9. A method of diagnosing primary congenital glaucoma in an individual, comprising detecting a change of nucleotide 1656 from C to T in the human cytoclrome P4501B1 gene, wherein the presence of the insertion is indicative of primary congenital glaucoma.

10. A method of diagnosing primary congenital glaucoma in an individual, comprising detecting a change of nucleotide 1751 from C to T in the human cytochrome P4501B1 gene, wherein the presence of the insertion is indicative of primary congenital glaucoma.

* * * * *